US008999701B2

(12) United States Patent
Liu

(10) Patent No.: US 8,999,701 B2
(45) Date of Patent: Apr. 7, 2015

(54) **INHIBITOR TOLERANT *SACCHAROMYCES CEREVISIAE* STRAIN**

(75) Inventor: Zonglin L. Liu, Peoria, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 1299 days.

(21) Appl. No.: 12/143,965

(22) Filed: Jun. 23, 2008

(65) Prior Publication Data

US 2009/0004726 A1 Jan. 1, 2009

Related U.S. Application Data

(60) Provisional application No. 60/937,517, filed on Jun. 28, 2007.

(51) Int. Cl.
*C12P 7/10* (2006.01)
*C12R 1/865* (2006.01)

(52) U.S. Cl.
CPC . *C12P 7/10* (2013.01); *C12R 1/865* (2013.01); *Y02E 50/16* (2013.01); *Y02E 50/17* (2013.01)

(58) Field of Classification Search
CPC ......... Y02E 50/16; Y02E 50/17; Y02E 50/10; C12P 7/10; C12P 17/04; C12P 2203/00; C12P 7/065; C12P 7/06; C12P 7/08; C12P 7/16; C12P 7/46; C12P 7/56; C12P 13/001; C12P 19/02; C12P 7/18; C12P 7/40; C12P 7/44; C12P 7/54; C12N 9/00; C12R 1/865
See application file for complete search history.

(56) References Cited

U.S. PATENT DOCUMENTS

| | | | | |
|---|---|---|---|---|
| 6,372,269 | B1 * | 4/2002 | Rangel-Aldao et al. | 426/62 |
| 7,067,303 | B1 * | 6/2006 | Nichols et al. | 435/254.1 |
| 7,253,001 | B2 * | 8/2007 | Wahlbom et al. | 435/471 |
| 2002/0192774 | A1 * | 12/2002 | Ahring et al. | 435/162 |

FOREIGN PATENT DOCUMENTS

WO 2005111214 A1 * 11/2005

* cited by examiner

*Primary Examiner* — Debbie K Ware
(74) *Attorney, Agent, or Firm* — John Fado; Albert Y. Tsui; Lesley Shaw

(57) ABSTRACT

Furfural and 5-hydroxymethylfurfural (HMF) are representative inhibitors to ethanologenic yeast generated from biomass pretreatment using dilute acid hydrolysis. Few yeast strains tolerant to inhibitors are available. A novel tolerant strain of *Saccharomyces cerevisiae*, NRRL Y-50049, having enhanced biotransformation ability to convert furfural to furan methanol (FM), HMF to furan di-methanol (FDM), and is able to produce a normal yield of ethanol as an initial culture.

7 Claims, 17 Drawing Sheets

HMF

FDM

Furfural

FM

INHIBITOR TOLERANT *SACCHAROMYCES CEREVISIAE* STRAIN

CROSS-REFERENCE TO RELATED APPLICATION

This application claims the benefit of the filing date of the U.S. Provisional Patent Application Ser. No. 60/937,517 filed on Jun. 28, 2007.

FIELD OF THE INVENTION

The present invention is for a novel ethanologenic yeast *Saccharomyces cerevisiae* strain having the characteristic of being tolerant to biomass conversion inhibitors. More specifically, the strain is able to in situ detoxify the inhibitors furfural and 5-hydroxymethylfurfural generated from biomass pretreatment via conventional dilute acid hydrolysis.

BACKGROUND OF INVENTION

Renewable biomass, including lignocellulosic material and agricultural residues such as corn fiber, corn stover, corn cob, wheat straw, rice straw, and sugarcane bagasse, are low cost materials for bioethanol production. However, significant challenges exist for sustainable and efficient conversion of biomass to ethanol. One barrier for the conversion of biomass to ethanol is the stress conditions involved in the biomass pretreatment process. Dilute acid hydrolysis is commonly used in biomass degradation which hydrolyzes cellulose and hemicellulose fractions to increase fiber porosity to allow enzymatic saccharification and fermentation of the cellulose fraction. (Saha, B. C., et al., 2003. *J. Ind. Microbiol. Biotechnol.,* 30:279-291). However, acid hydrolysis of biomass generates inhibitory compounds that interfere with microbial growth and hinders subsequent fermentation. For example, the resultant hydrolysate from dilute acid pretreatment comprises of a complex mixture, in which more than 35 potentially toxic ethanologenic inhibiting compounds have been identified. (Luo, C., et al., 2001. *Biomass Bioenergy* 22:125-138). These compounds can be divided into four main groups of aldehydes (such as furfural, 5-hydroxymethylfurfural, etc.), ketones, phenols, and organic acids (such as acetic, formic, levulinic acids, etc.). A remeditation process is needed to remove the inhibitors before the hydrolysate can be used for microbial growth and fermentation Two of the most potent inhibitors are furfural and 5-hydroxymethylfurfrual (5-hydroxymethylfurfrual referred to as "HMF" hereafter). During sugar degradation, pentose dehydration leads furfural build up while hexose dehydration leads to HMF build up. These two inhibitory compounds reduce enzymatic biological activities, break down DNA, inhibit protein and RNA synthesis (Modig, T., et al. 2002. *Biochem J.,* 363:769-776). Yeast can be repressed by the inhibitory complex as low as a 5 mM combination of furfural and HMF (Liu, Z. L., et al., 2004. *J Ind Microbiol Biotechnol.,* 31:345-352). Most yeast strains, including industrial strains, are susceptible to the complexes associated with dilute acid hydrolysis pre-treatment (Martin, C., et al., 2003. *Enzy. Micro. Technol.,* 32:386-395). Yet few yeast strains tolerant to inhibitors are available and the need for tolerant strains is well recognized (Klinke, H. B., et al., 2004. *Appl. Microbiol. Biotechnol.,* 66:10-16 and Zaldivar J., et al., 2001. *Appl. Microbiolo. Biotechnol.,* 697 56:17-34).

To facilitate fermentation processes using existing yeast strains, additional remediation treatments are required. Such treatments including physical, chemical, or biochemical detoxification procedures are utilized to remove these inhibitory compounds. For example, U.S. Pat. No. 4,461,648 describes a steam cooking method wherein lignocellulosic material is fed in a pressurized steam vessel and optimized with volatiles vented from the vessel. Additionally, U.S. Pat. No. 6,090,595 describes a pretreatment method of cellulosic feedstock wherein the ratio of [arabinan plus xylan] to [xylan plus arabinan plus cellulose] is utilized for ethanol production. Additional methods for hydrolysate detoxification include the addition of ion exchange resins (Nilvebrant, N. O., et al., 2001. *Appl. Biochem. Biotechnol.,* 91/93:35 49), addition of active charcoal (Gong, C. S., et al., 1993. *Appl. Biochem. Biotechnol.,* 39/40:83 88), enzymatic detoxification of hydrolysate using laccase and lignin peroxidase (Jonsson, L. J., et al. 1998. *Appl. Microbiol. Biotechnol.,* 49:691-697), overliming (Martinez, A., et al. 2001. *Biotechnol. Prog.,* 17:287-293), increasing yeast inoculum (Chung, I. S., et al. 1985. *Biotechnol Bioeng.,* 27:308-315). However, these additional steps present additional complexity to the production of bioethanol production, produces waste products, and adds significantly to overall cost production. As such there is a need in to the art to engineer a yeast strain that is tolerant to inhibitors resulting from an economic hydrolysis pre-treatment process, circumventing remediation treatments.

It has been demonstrated that ethanologenic yeast individual strains of *Saccharomyces cerevisiae* can withstand and in situ detoxify furfural or HMF. (Liu, Z. L., et al., 2005. *Appl. Biochem. Biotechnol.,* 121-124:451-460 and Liu, Z. L., et al. 2004. *J. Ind. Microbiol.* Biotechnol., 31:345-352). However, these strains are tolerant to a single inhibitor of either furfural or HMF, but not to both. As such, there is a need in the art for a *Saccharomyces* yeast strain that is tolerant of both inhibitors.

BRIEF SUMMARY OF THE INVENTION

An embodiment of this invention is a novel strain of *Saccharomyces cerevisiae* yeast which can in situ covert furfural and 5-hydroxymethylfurfural (HMF) by accelerated aldehyde reduction, wherein said strain referred to as 12HF10 and deposited as NRRL-Y-50049 on Jun. 20, 2007 under the provisions of the Budapest Treaty, with the U.S.D.A. Agricultural Research Service Patent Culture Collection (National Center for Agricultural Utilization Research, 1815 N. University Street, Peoria, Ill. 61604).

Another embodiment of the invention is a culture comprising agricultural biomass acid hydrolysate and a strain of yeast, wherein said hydrolysate comprises furfural and HMF, wherein said yeast is capable of reducing the level of said furfural and HMF by in situ aldehyde reduction. It is contemplated that the agricultural biomass is a woody material of cellulosic or lignocellulosic plant material selected from the group consisting of orchard prunnings, chaparral, mill waste, urban wood waste, municipal waste, logging waste, forest thinnings, short-rotation woody crops, and industrial waste. It is also contemplated that agricultural biomass comprise of nonwoody material such as gramineous agricultural residue. The nonwoody material is selected from the group consisting of wheat straw, oat straw, rice straw, barley straw, rye straw, flax straw, sugar cane, corn stover, corn stalks, corn cobs, corn husks, prairie grass, gamagrass, and foxtail. It further contemplated that the nonwoody material is selected from the group consisting of sugar beet pulp, citrus fruit pulp, seed hulls, cellulosic animal wastes, lawn clippings, and seaweed.

It is contemplated that the novel yeast strain be utilized for the treatment of polysaccharide material such as cellulose, hemicellulose, and lignocellulose by hydrolysis to produce monosaccharides such as pentose and hexoses. It is further contemplated that the resulting pentose or hexose fermented for the production of bioethanol from the monosaccharides. Additionally, the novel strain can be utilized be used for cellulosic ethanol conversion after processing of high valued 5-carbon products using the processing residues.

It is also further contemplated that the novel strain be utilized in tandem with other yeast strains for bioethanol production, wherein the novel strain would detoxify the inhibitors and use hexoses and a second strain would ferment the pentoses for ethanol production.

BRIEF DESCRIPTION OF THE DRAWING

The present invention together with the above and other objects and advantages may best be understood from the following detailed description of the embodiment of the invention illustrated in the drawings, wherein:

FIGS. 2*a*. and 2*b*. depict Y-12632 response to 0 mM HMF, FIGS. 2*c*. and 2*d*. at 10 mM HMF, FIGS. 2*e* and 2*f*. at 30 mM HMF, FIGS. 2*g*. and 2*h*. at 60 mM HMF, and FIGS. 2*i*. and 2*j*. at 120 mM HMF. Figure legends for FIGS. 2*b*, 2*d*, 2*f*, 2*h*, 2*j* depict HPLC assay data labeled as glucose (●), ethanol (○), HMF (▲) and FDM (Δ) amounts as a function of time. Glucose and ethanol amounts were estimated by g/L; HMF and FDM remaining amount is presented by mM.

DEPOSIT OF BIOLOGICAL MATERIAL

Figure 1:
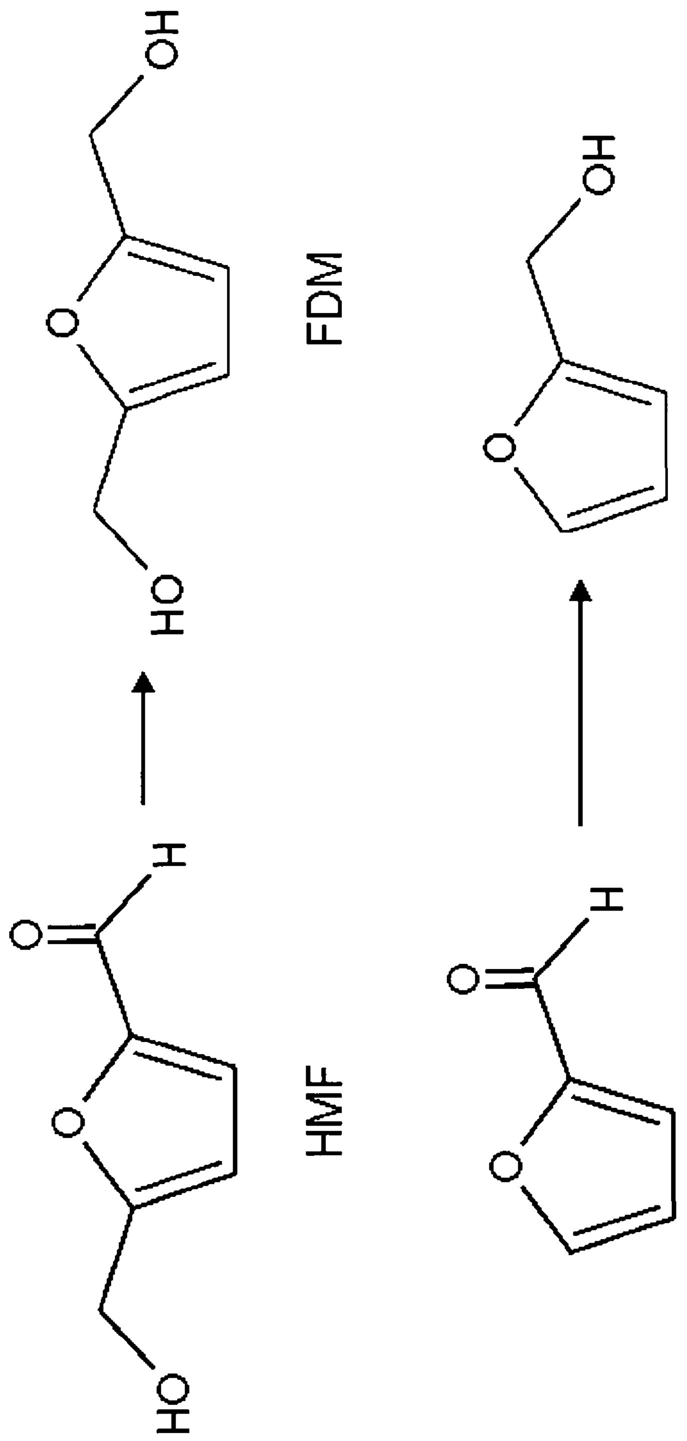
FIG. 1. depicts metabolic conversion products of inhibitors. Furfural is converted into 2-furanmethanol (FM, furfuryl alcohol) and 5-hydroxymethylfurfural (HMF) is converted into 2,5-furan dimethanol (FDM; 2,5-bis-hydroxymethylfuran). Furfural has been studied intensively and furfural conversion to FM by yeasts has been established. Conversely, HMF degradation has been commonly observed however the mechanisms for its conversion are not clear until the identification of FDM (Liu, Z. L., et al. 2004. *J. Ind. Microbiol. Biotechnol.,* 31:345-352).

The novel inhibitor tolerant strain, identified as a strain of *Saccharomyces cerevisiae*, was deposited on Jun. 20, 2007, under the provisions of the Budapest Treaty in the Agricultural Research Culture Collection (NRRL) in Peoria, Ill., and has been assigned Accession No. NRRL Y-50049.

DETAILED DESCRIPTION OF THE INVENTION

Definitions

As used in the specification and claims, the singular form "a", "an" and "the" include plural references unless the context clearly dictates otherwise. For example, the term "a cell" includes a plurality of cells, including mixtures thereof.

The term "inhibitors" refers to any inhibitory generated from lignocellulose hydrolysates that inhibits ethanologenesis. Inhibitors comprise of aliphatic acids, furaldehydes, aromatic compounds and extractives. Aliphatic acids, such as acetic, formic and levulinic acid, are formed as degradation products from carbohydrates. Furaldehydes, such as furfural and 5-hydroxymethylfurfural (HMF), are also derived from hydrolysis of pentose sugars and hexose sugars respectively. Additionally, inhibitors such as furfural and HMF, and cinnamaldehyde are classified as aldehyde inhibitors inasmuch as the furan ring is not the cause of toxic effect of wild type yeast strains.

"Agricultural biomass" is defined herein to mean any cellulosic or lignocellulosic plant material, especially waste material, including but not limited to, leaves and stalks of both woody and non-woody plants. The term "woody" is used herein both in the botanical sense to mean "comprising wood"; that is, composed of extensive xylem tissue as found in trees and shrubs, and also in the sense of "being woodlike". Accordingly, "nonwoody" refers to materials lacking these characteristics.

Agricultural biomass from woody plants would include orchard prunnings, chaparral, mill waste (such as bark, chips, shavings, sawdust, and the like), urban wood waste (such as discarded lumber, wood pallets, crates, tree and brush trimmings, etc.), municipal waste (such as newspaper and discarded grocery produce), logging waste and forest thinnings (tree tops, limbs and cull material), short-rotation woody crops such as poplar and cottonwood, and industrial waste (such as wood pulp sludge).

The preponderance of biomass from non-woody plants is derived from monocotyledonous plants, and especially grassy species belonging to the family Gramineae. Of primary interest are gramineous agricultural residues; that is, the portion of grain-bearing plants that remain after harvesting the seed. Illustrative of such residues, without limitation thereto, are wheat straw, oat straw, rice straw, barley straw, rye straw, flax straw, sugar cane, corn stover, corn stalks, corn cobs, corn husks, and the like. Also included within this definition are grasses not conventionally cultivated for agricultural purposes, such as prairie grasses (e.g. big bluestem, little bluestem, Indian grass), switchgrass, gamagrass, and foxtail.

Moreover, byproducts of agriculture industrial process have high amounts of furfural and HMF. For example, corncobs are used to produce xylose and furfural in certain countries, including China. For economic reasons, corncobs are treated by acid hydrolysis with byproduct residues from such production considered waste product inasmuch as inhibitors such as furfural are present. Such waste processing residues are usually burned. However, a significant amount of cellulose exists in the corncob residues that can be used to convert into ethanol.

Other agricultural byproducts in the category of biomass include waste streams components from commercial processing of crop materials (such as sugar beet pulp, citrus fruit pulp, seed hulls, and the like), cellulosic animal wastes, lawn clippings, seaweed, etc.

Any of the aforementioned biomass materials would be utilizes as substrates for fermentative conversion to ethanol. The term "agricultural biomass hydrolysate" or variations thereof is used herein to refer to any of the aforementioned biomass materials that have been pretreated with acid to solubilize the xylan and cellulose in the material and to release sugar monomers. The hydrolysate may have residual xylan or may have been treated to remove the xylan.

The following non-limiting examples are provided to further illustrate various embodiments of the present invention.

Yeast, Medium, Growth Conditions, and Inhibitor Treatment

Wild type *Saccharomyces cerevisiae* was obtained from Agricultural Research Service Culture Collection (Peoria, Ill. USA) (NRRL Y-12632). Additionally a novel furfural and HMF tolerant strain, 12HF10, (deposited as NRRL Y-50049) was utilized. Both yeast cultures of Y-2632 and Y-50049 were maintained on a synthetic medium and pre-cultures. Briefly, yeast strains were maintained on YM agar (3 gm yeast extract, 3 gm malt extract, 5 gm peptone, 20 g agar in 1 liter of distilled water) after their recovery from a lyophilized form. Stock cultures were kept at −80° C. in YM broth amended with 30% glycerol.

Cultures were routinely maintained on a synthetic complete medium consisting of 6.7 gm yeast nitrogen base without amino acids and 20 gm dextrose supplemented with 16 amino acids. The amino acid components were added into the medium aseptically at the final concentrations (per 1) of 20 mg adenine sulfate, 20 mg uracil, 20 mg L-tryptophan, 20 mg L-histidine hydrochloride, 20 mg L-arginine hydrochloride, 20 mg L-methionine, 30 mg L-tyrosine, 30 mg L-leucine, 30 mg L-isoleucine, 30 mg L-lysine hydrochloride, 50 mg L-phenylalanine, 100 mg L-glutamic acid, 100 mg L-aspartic acid, 150 mg L-valine, 200 mg L-threonine, and 400 mg L-serine.

When solid medium was prepared, agar was autoclaved and the sterilized components added afterward. A loopful of cells of each strain from the synthetic medium agar plate was transferred into a synthetic broth and incubated at 30° C. with agitation and maintained in the broth prior to inoculum preparation. Cells were harvested by centrifugation 8-15 hours after incubation and suspended in a fresh synthetic broth serving as the inoculum source. The initial OD at 620 nm of the inoculated medium for each culture was adjusted and recorded. Each strain was grown in a 15-ml test tube containing 3 ml of synthetic broth amended with inhibitory compounds in an incubator at 30° C. with agitation at 220 rpm under micro-oxic conditions. Cell growth was monitored by measuring optical absorbance at 620 nm using a spectrophotometer and samples were taken periodically.

For inhibitor application, cultures were supplemented with HMF at a series of final concentrations of 0, 10, 30, 60, and 120 mM, or combined inhibitors of furfural and HMF each at 12 mM, respectively. A non inhibitor treated culture served as a control. Cultures were monitored for cell growth at $OD_{600}$ and samples were taken hourly for the first 16 hours and proper intervals afterward till the completion of the fermentation. Cell free supernatant was taken for metabolic profiling analysis using HPLC. A chemical standard of HMF conversion product was synthesized as described infra. Duplicated experiments were carried out for all treatments.

Strain Y-50049 was derived from parent strain Y-12632 via survival mutants adapted to survive selection condition of inhibitor stress while maintain desirable fermentation and ethanol production characteristics. Using this method, strains were first grown in a synthetic medium containing lower concentrations of furfural and/or HMF. Once logarithmic growth phase was reached, cells were transferred into a fresh medium broth supplemented with inhibitors. Cultures were monitored and subsequently transferred iteratively in the same manner. As the adapted cultures became stable, inoculum levels were gradually reduced. Once the adapted culture was established, it was then introduced into a medium with a higher concentration of inhibitors. This iterative process was upgraded to higher inhibitor concentrations until a desirable tolerance level was reached. The selection and subculture transferring were carried out 400-500 generations to obtain a relative uniform and stable population. Stable cultures were maintained using no more than 1% of inoculum (v/v) in the respective inhibitory medium and stored in the synthetic broth with glycerol at −80° C.

HPLC Analysis

Metabolic kinetics including glucose consumption, ethanol production, furfural and HMF reduction, and FM and FDM formation were assayed using a Waters HPLC equipped with either an Aminex Fast Acid column or an Aminex HPX-87H column (Bio-Rad Laboratories, Hercules, Calif.) and a refractive index detector. The column was maintained at 65° C. and samples eluted with 5 mM $H_2SO_4$ at 0.6 ml/min. The HPLC analysis was standardized using solutions of pure compounds obtained from Sigma-Aldrich, with the exception of FDM. Briefly, HMF was prepared by sodium borohydride reduction of HMF. Sodium borohydride (0.1667 g, 4.407 mmol) was added to a 50 ml round bottom flask with 10 ml of absolute ethanol. The suspension was cooled in an ice bath for 15 minutes and then 1.0278 g of HMF (8.150 mmol) was added in 4 ml of ethanol. A flask containing the HMF was washed twice with 1 ml portions of ethanol and the washings were added to the reaction flask. The reaction mixture was stirred at 0° C. for 2 hours and then warmed to room temperature and stirred for an additional 22 hours. To the reaction mixture were added 5 ml of $H_2O$ and a few drops of 1M HCl to destroy the remaining $NaBH_4$. Then 2M NaOH was added to take the pH back to approximately 7, and the resulting solution was stirred for 30 minutes at room temperature. The aqueous solution was extracted with diethyl ether (4×30 ml). The extracts were dried with $Na_2SO_4$, filtered, and concentrated. Purification by flash chromatography (1:1 ethylacetate: hexane as an eluent) gave 0.738 g (71%) of a slightly yellow solid whose $^1H$ NMR and MS spectra matched those previously reported for FDM. The sample purity is greater than 95% by NMR spectroscopy.

EXAMPLE 1

Dose-Dependent Response of Ethanologenic Yeast

Figure 2A:
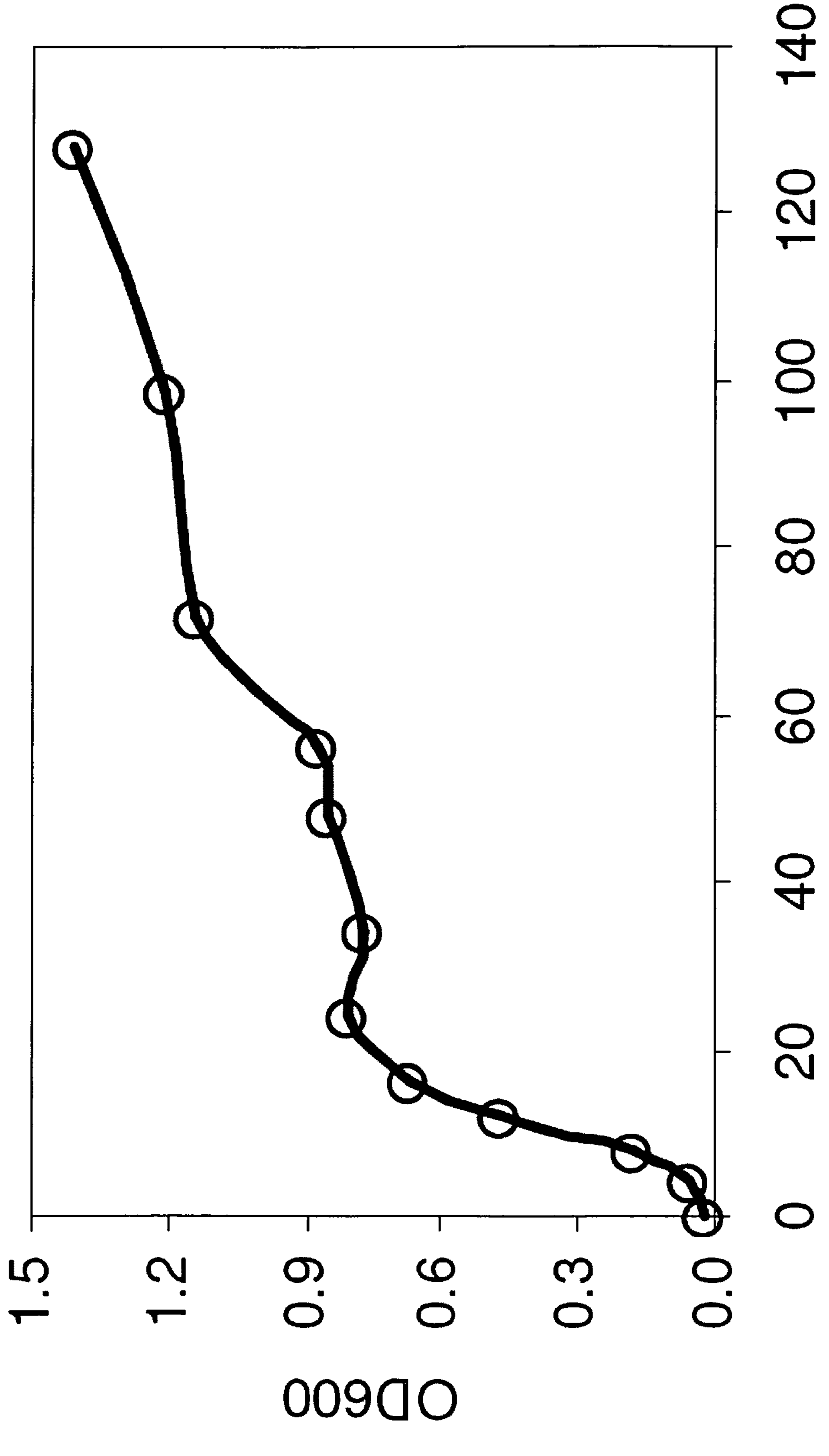
FIGS. 2*a*., 2*c*., 2*e*., 2*g*., and 2*i*. depict various graphs of dose-dependent response of *Saccharomyces cerevisiae* NRRL Y-12632, a wild type of ethanologenic yeast, to HMF of cell growth as measured by $OD_{600}$ as a function of time (hours).
Figure 2B:
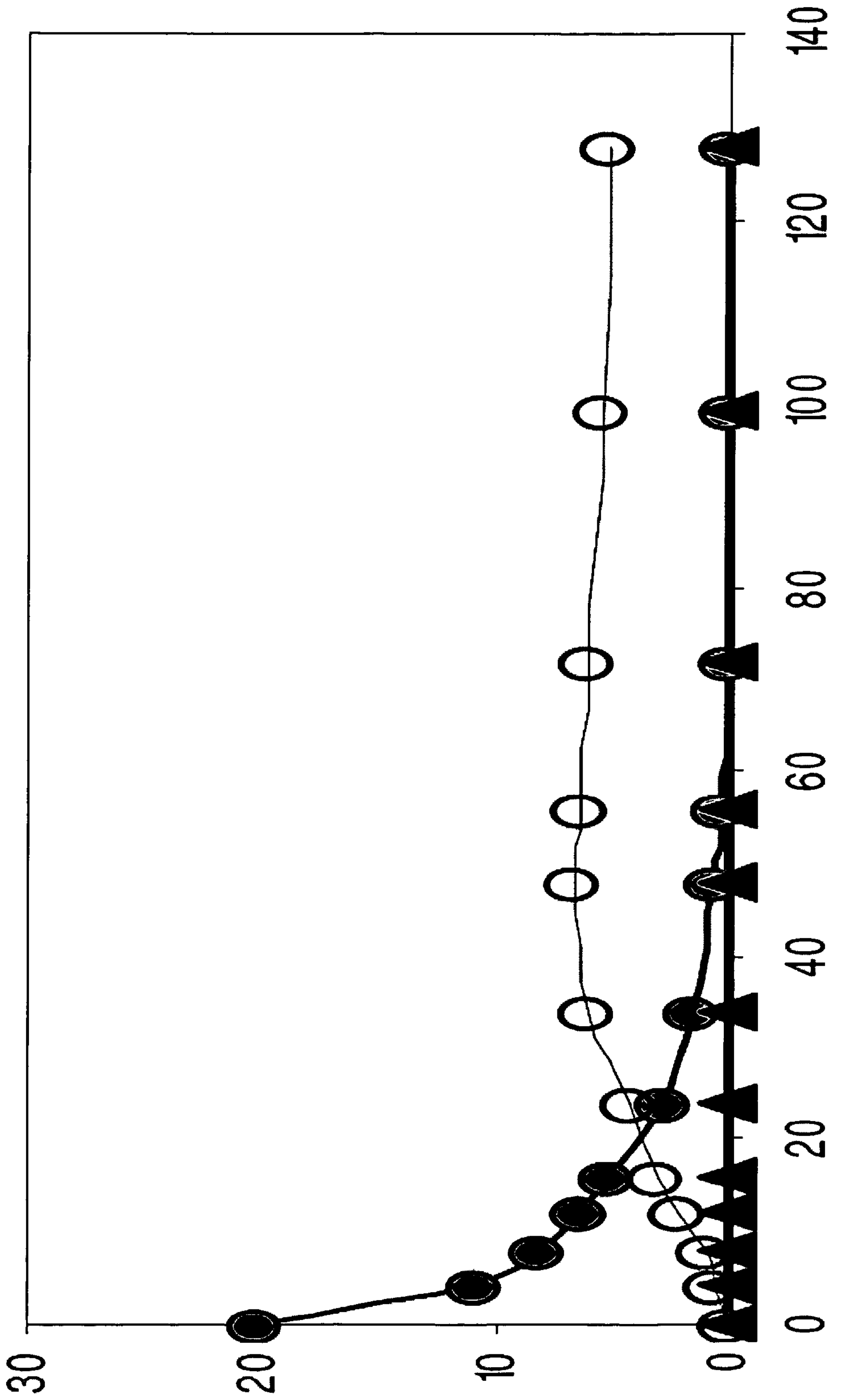
FIGS. 2*b*., 2*d*., 2*f*., 2*h*., and 2*j*. depict various graphs of glucose and ethanol expressed as g/L as a function of time.
Figure 2C:
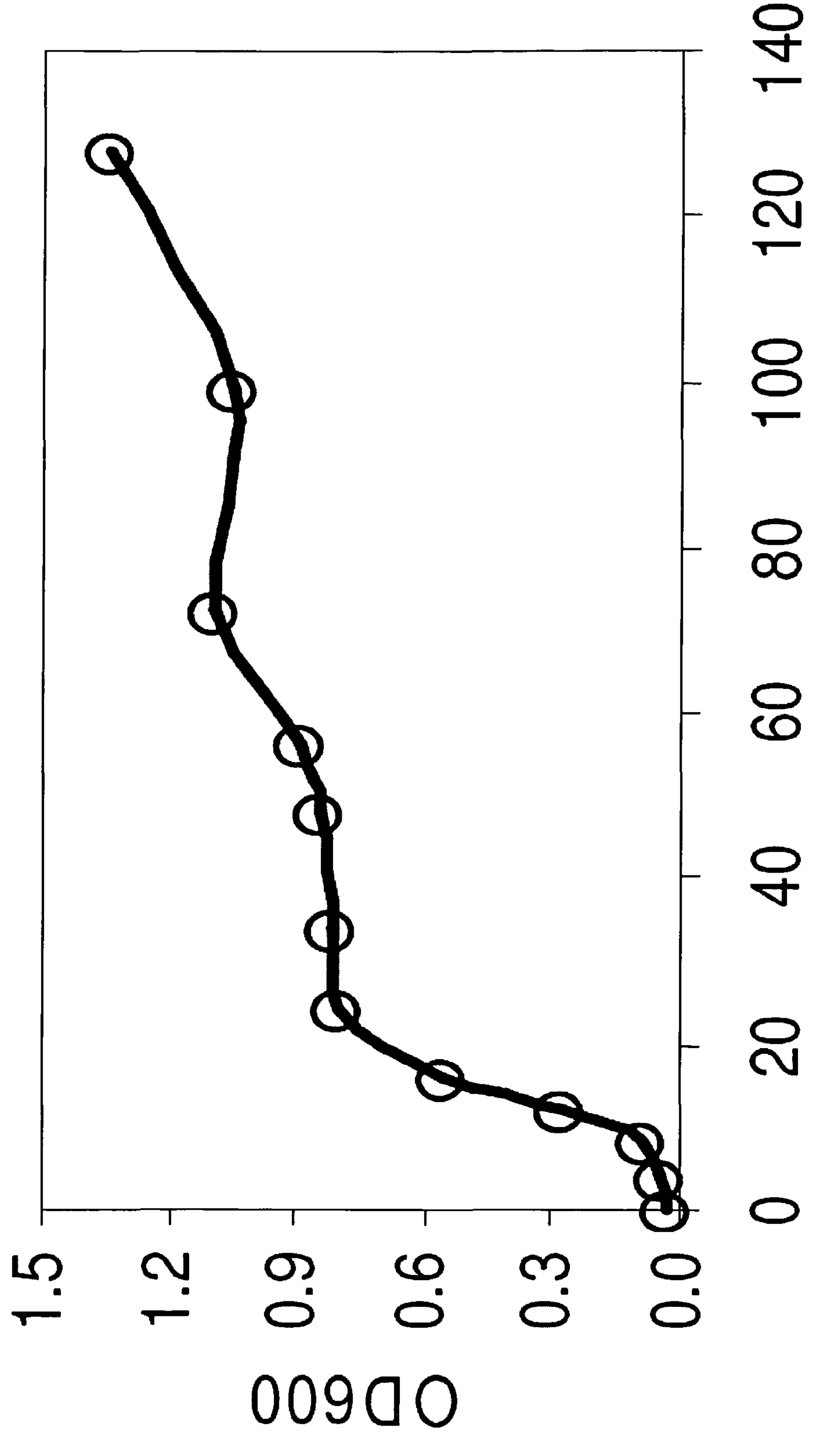
Figure 2D:
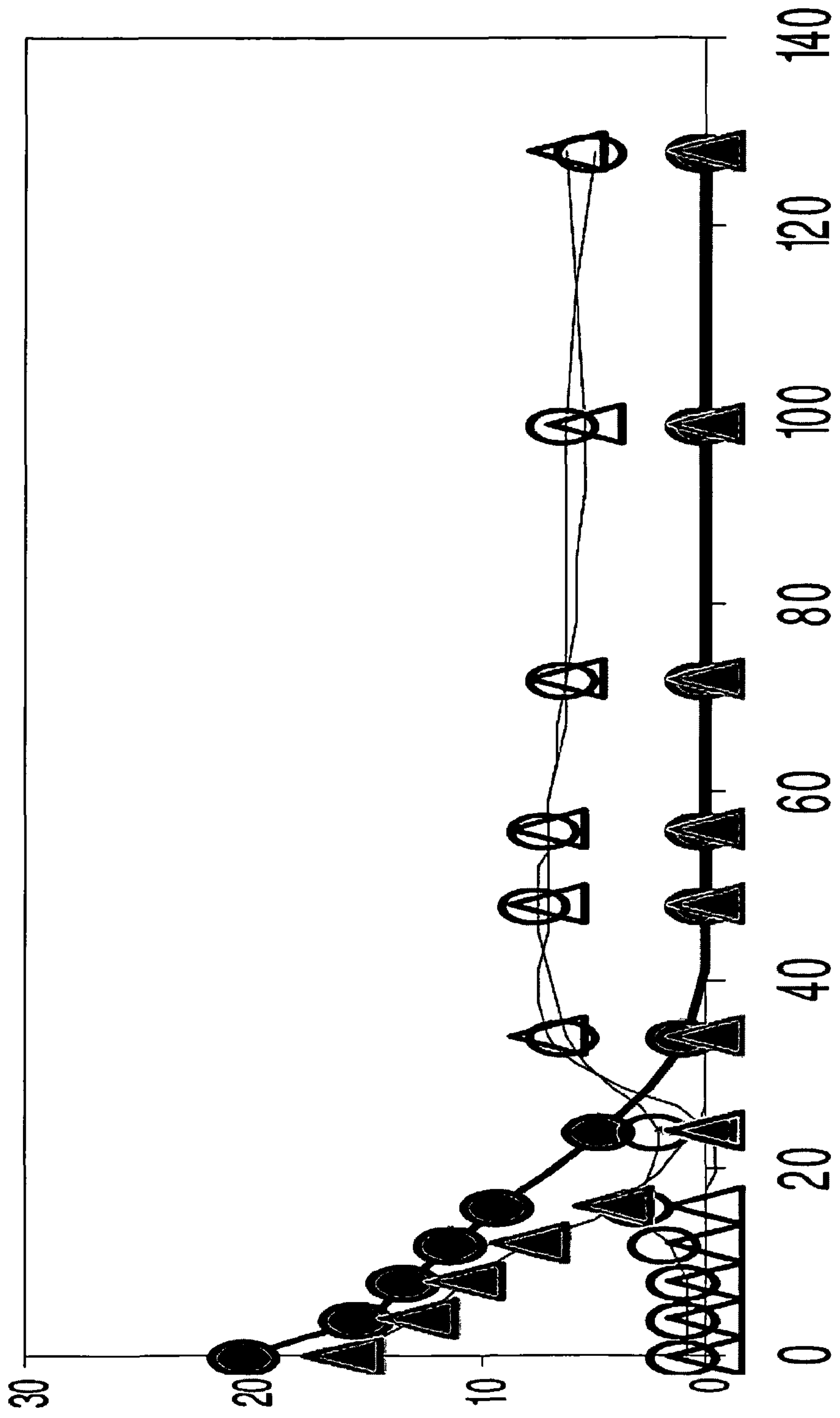
Figure 2E:
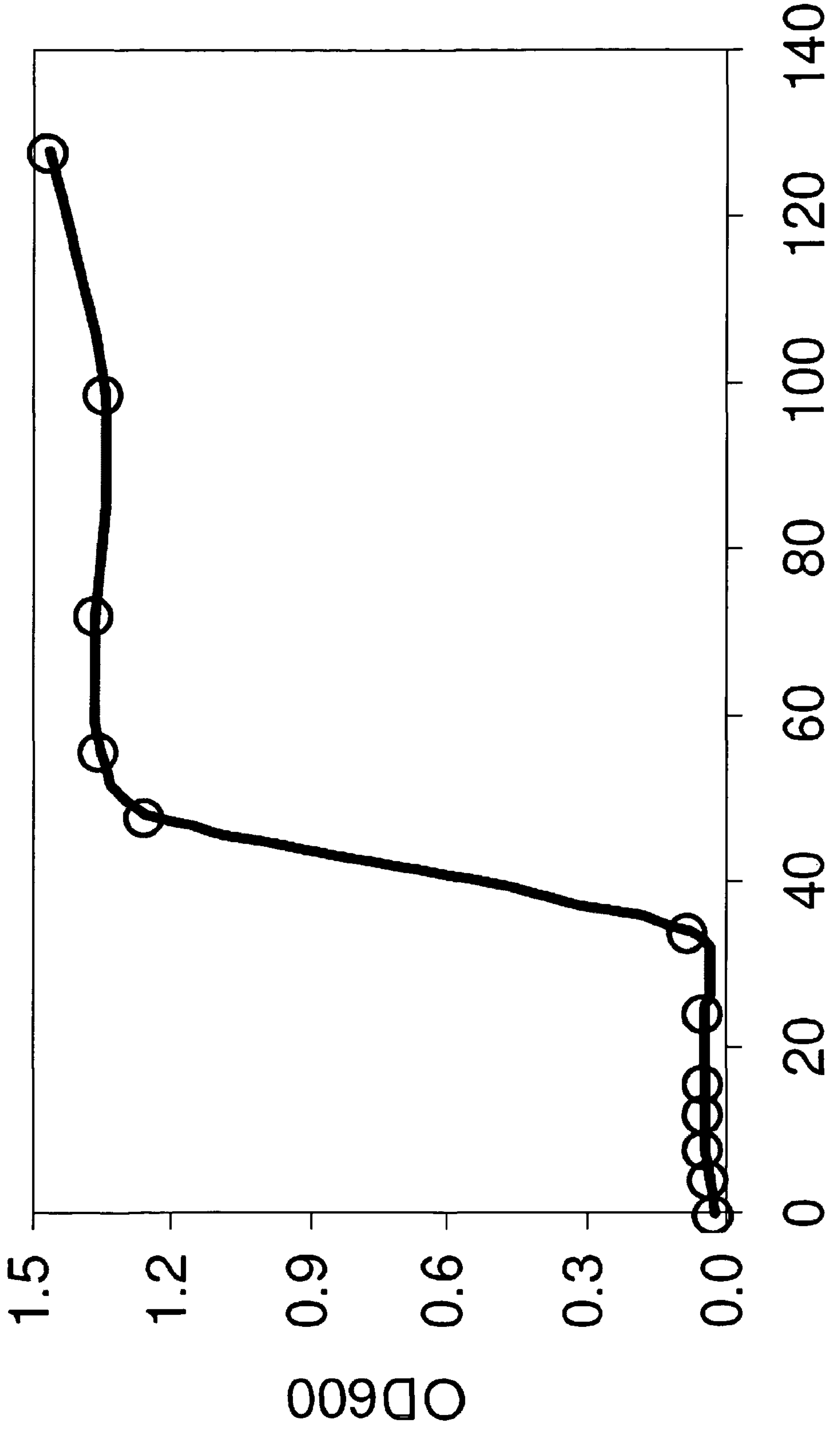
Figure 2F:
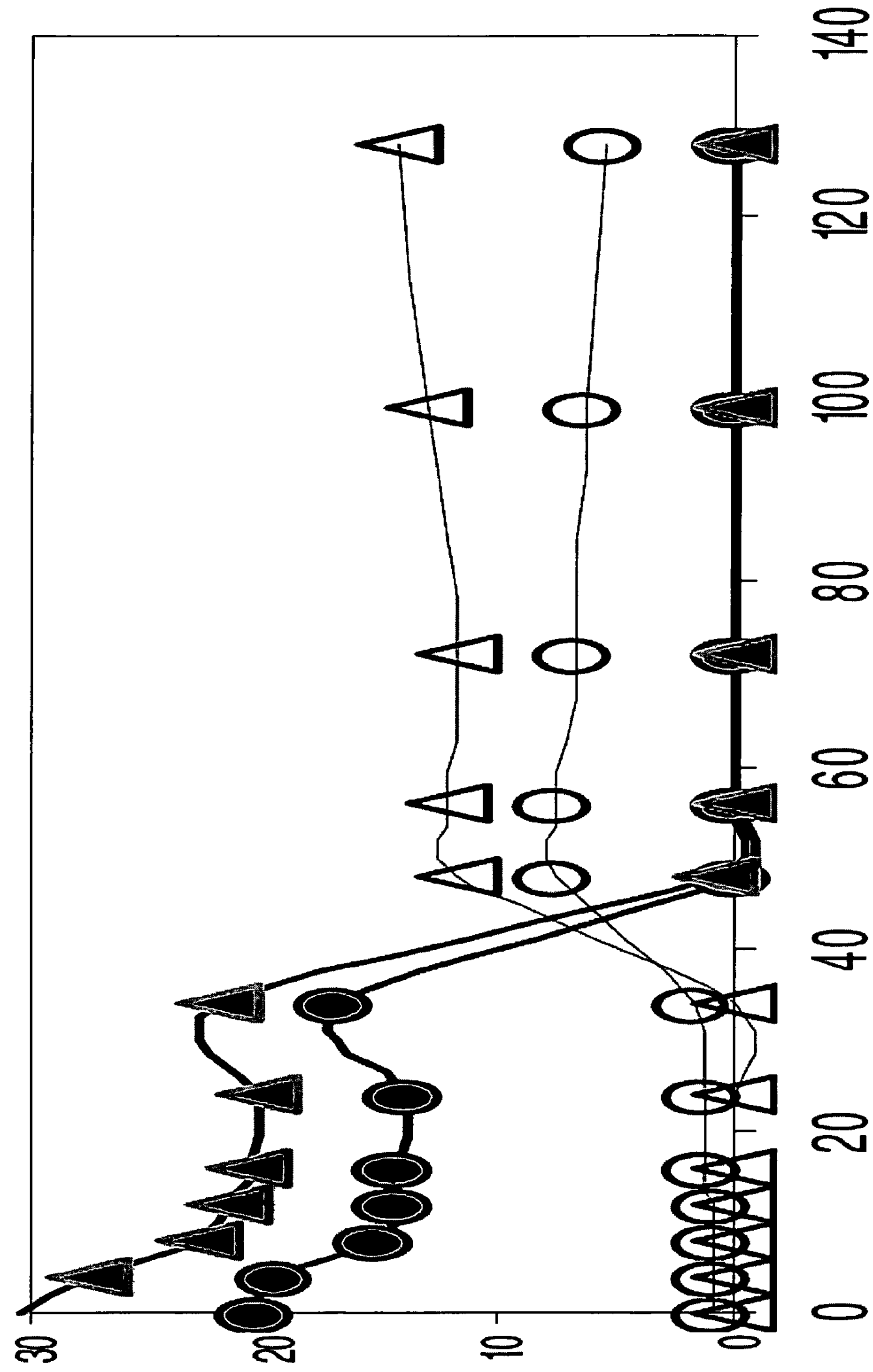
Figure 2G:
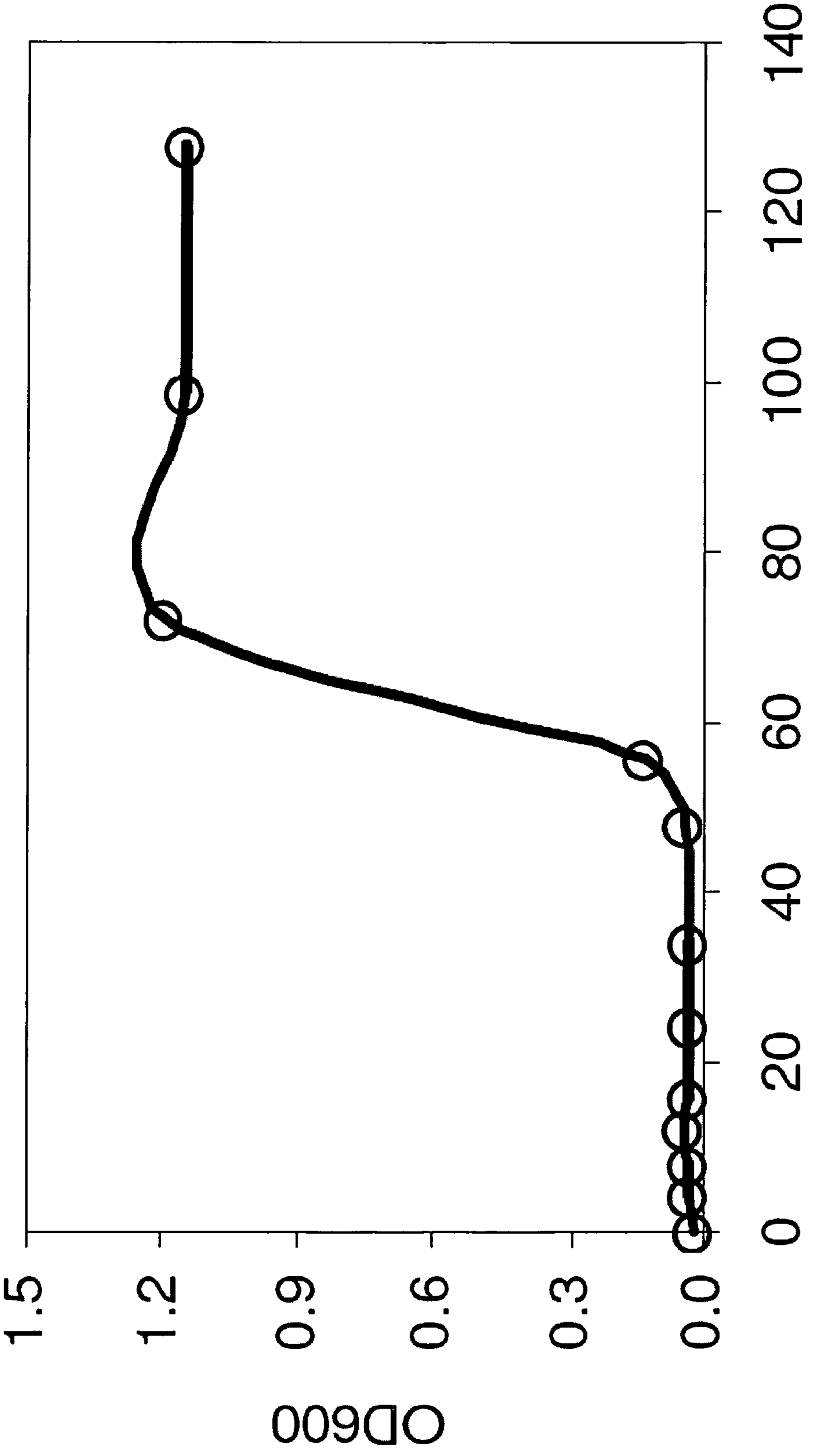
Figure 2H:
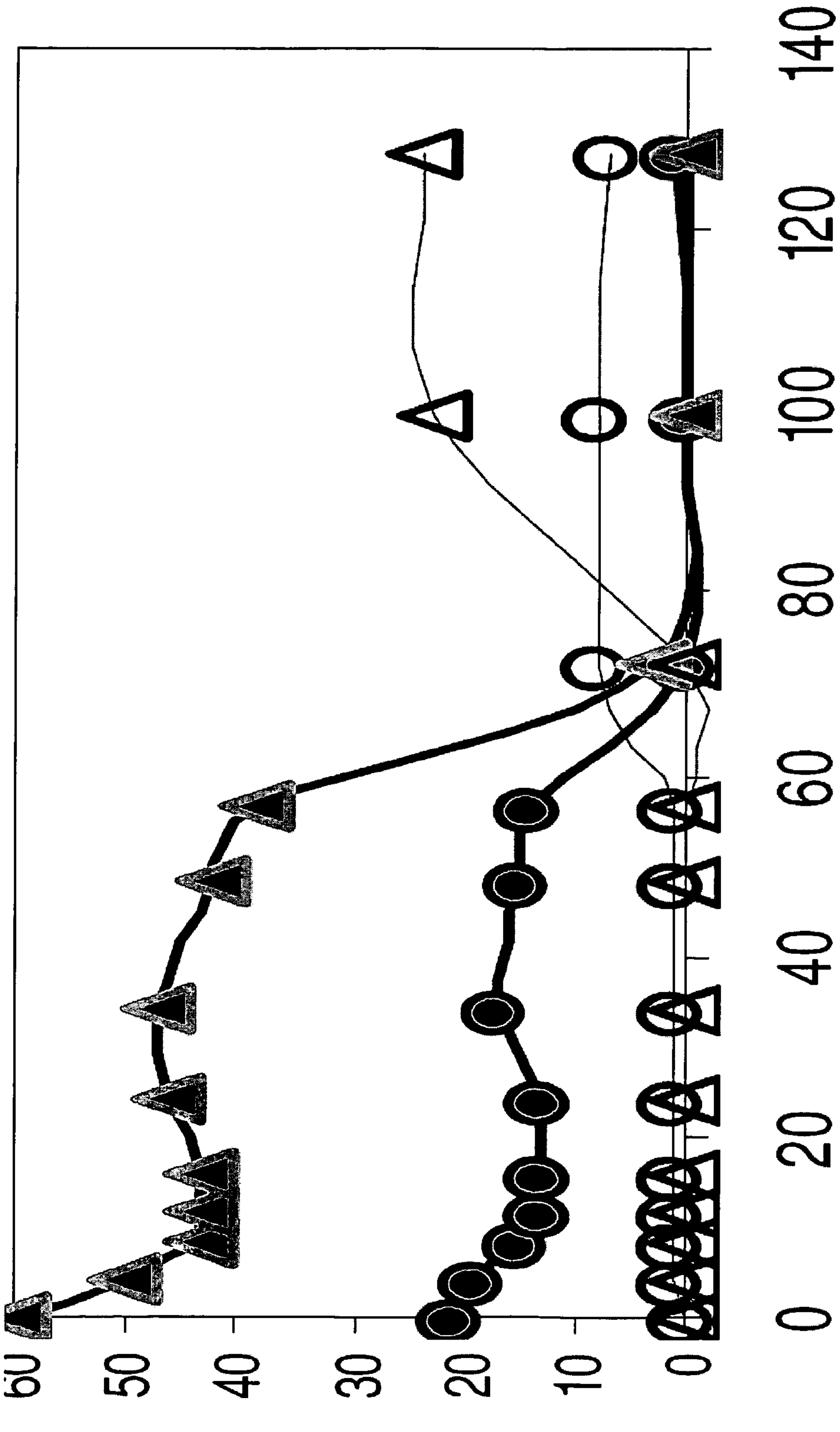
Figure 2I:
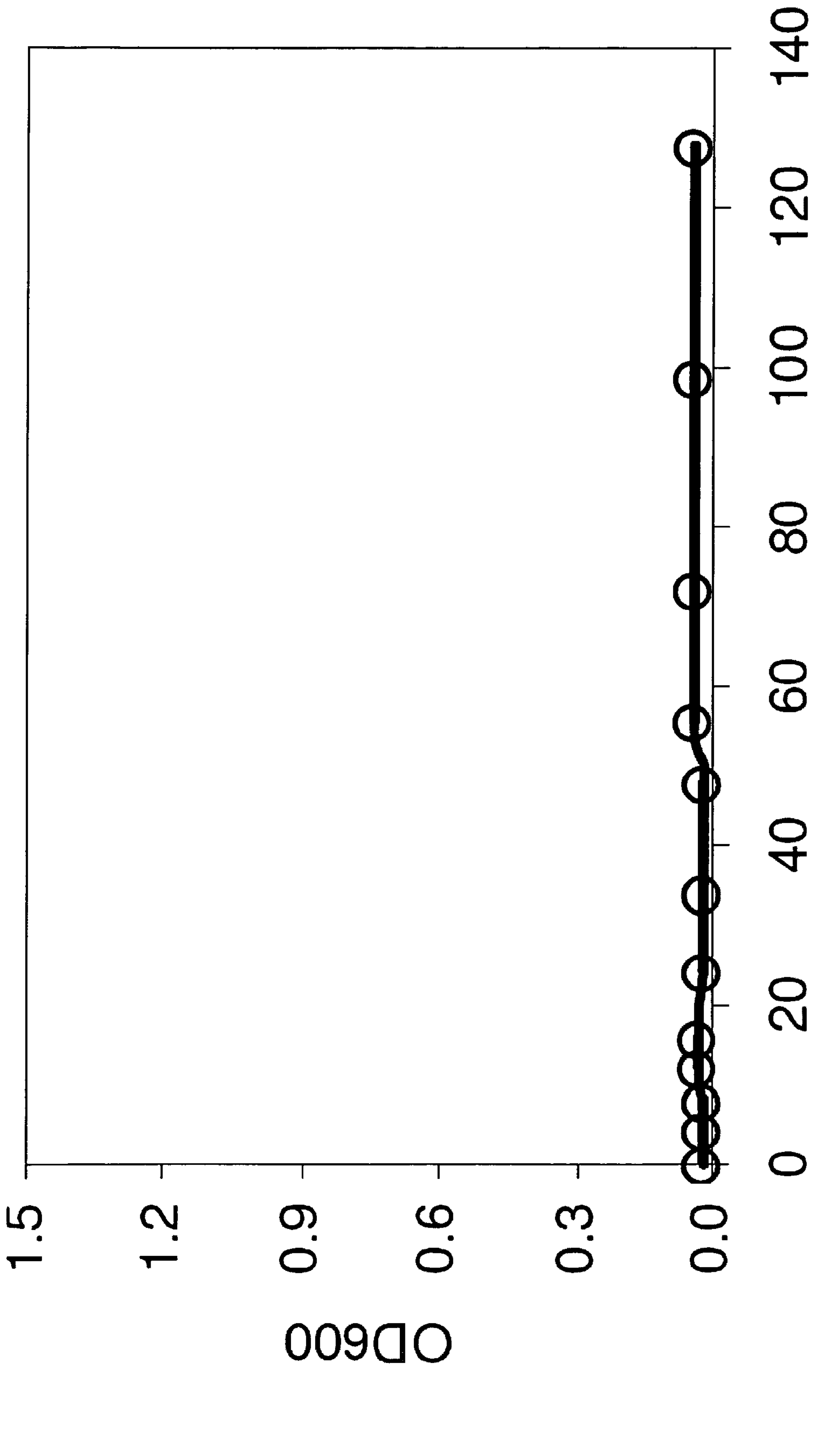
Figure 2J:
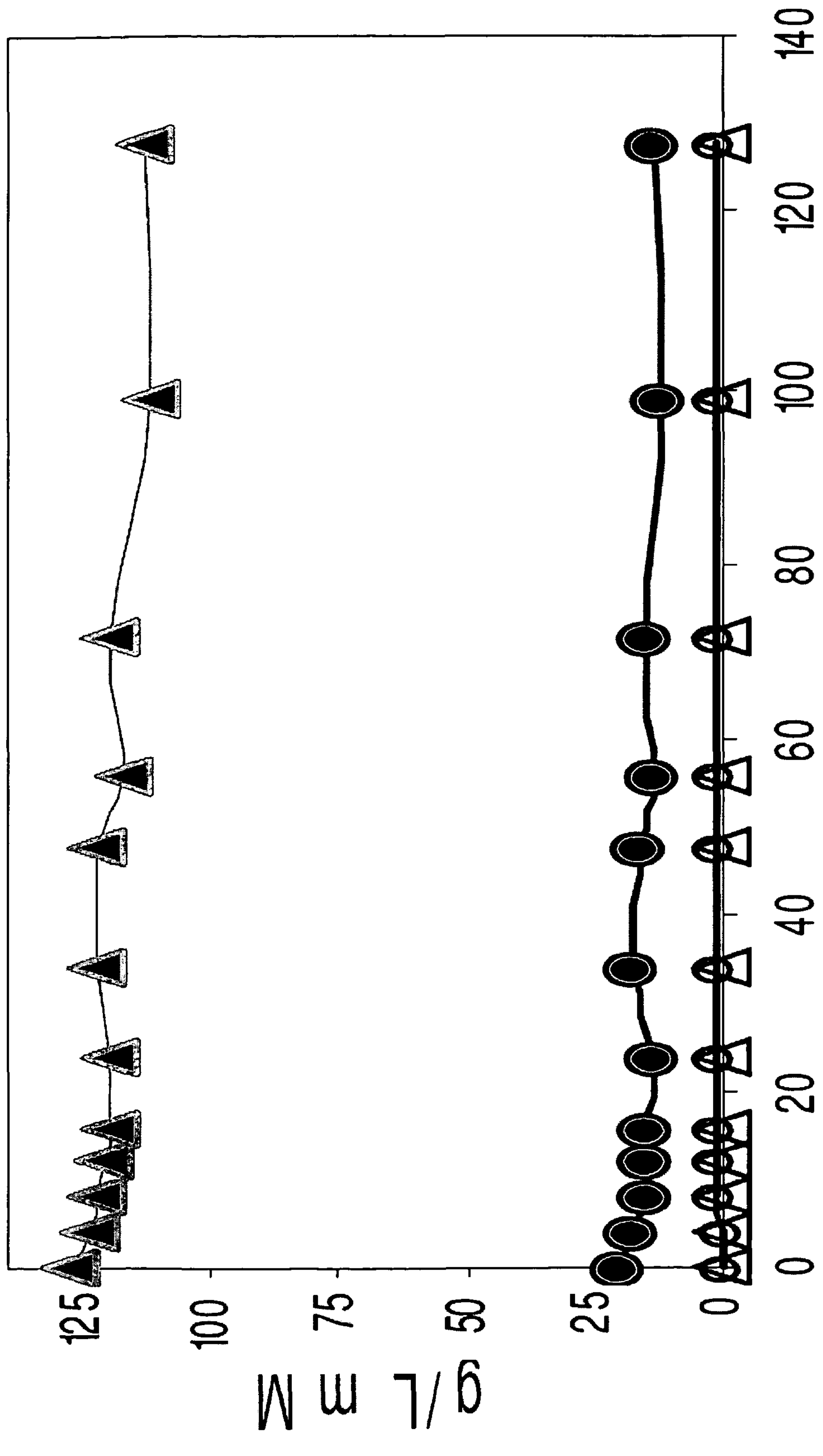

On the medium defined supra., strain Y-12632 showed clear dose-dependent cell growth and metabolic conversion activities in response to varied doses of HMF under controlled conditions. In the presence of HMF, cell growth was delayed under tolerable concentrations of 10, 30 and 60 mM compared with that of a control (FIGS. 2A, C, E, and G). At 120 mM, no cell growth was observed (FIG. 2I). Metabolic conversion activities to transform HMF to FDM and glucose to ethanol showed a similar trend of delay with the increase of HMF concentrations compared with the control. The HMF tolerance response was displayed as a lag phase not only for glucose consumption but also for ethanol conversion and HMF transformation. Once cell growth was recovered and metabolic activities resumed, FDM was detectable and persisted at the end of the fermentation at 128 h (FIGS. 2D, F, and H). However, this lag phase was not observed at a higher concentration of 120 mM FIG. 2J). At this lethal dose cells were completely repressed, and no biological activity or HMF transformation was observed till 128 hours after incubation.

In Situ Detoxification of Furfural and HMF by Strain NRRL Y-50049

Figure 3:
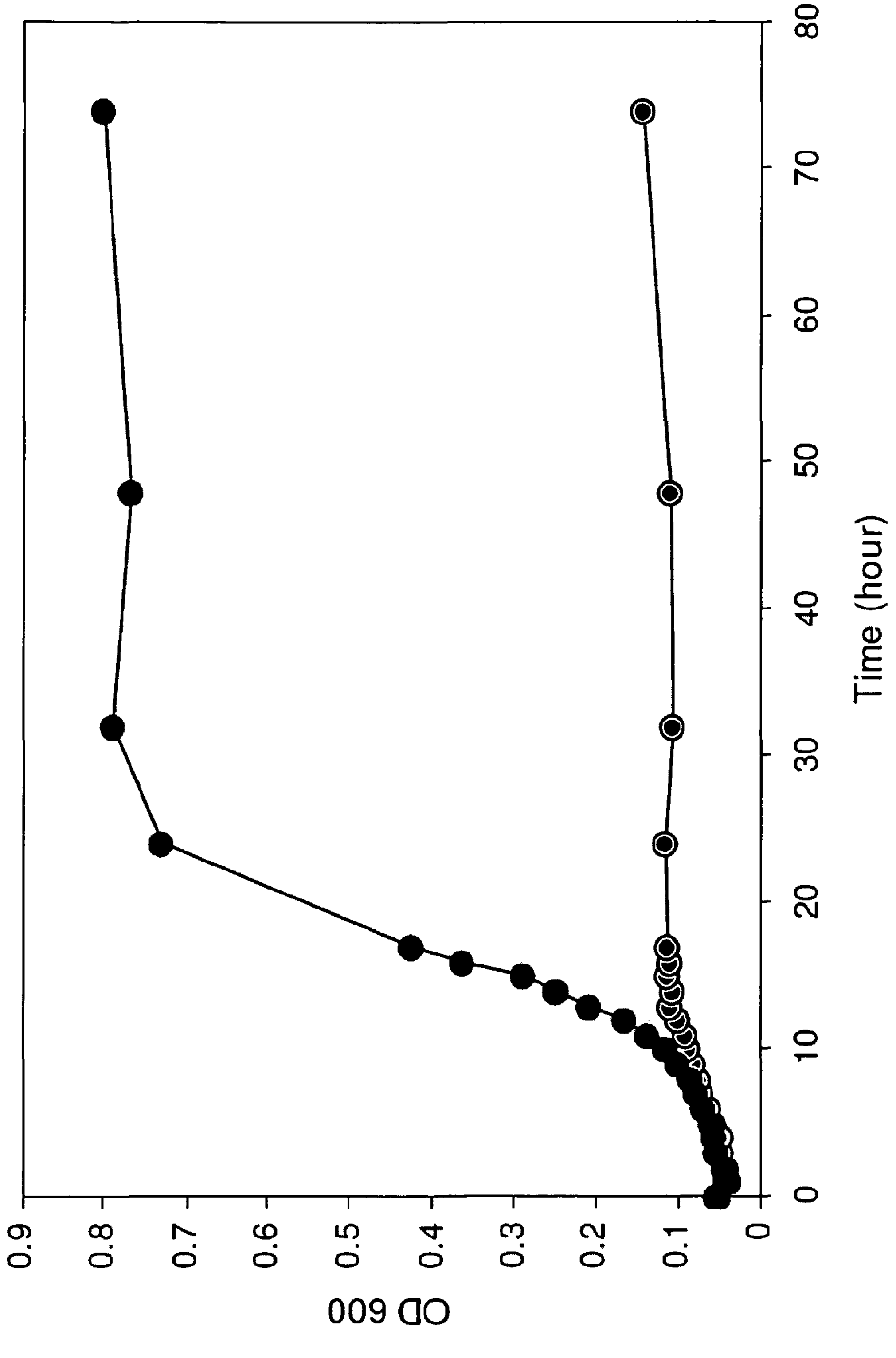
FIG. 3. depicts a graph of *Saccharomyces cerevisiae* NRRL Y-12632 (○) and strain NRRL Y-50049 (●) cell grow measured by $OD_{600}$ in response to furfural and HMF each at 12 mM as a function of time (hours) on a yeast medium as described infra.
Figure 4A:
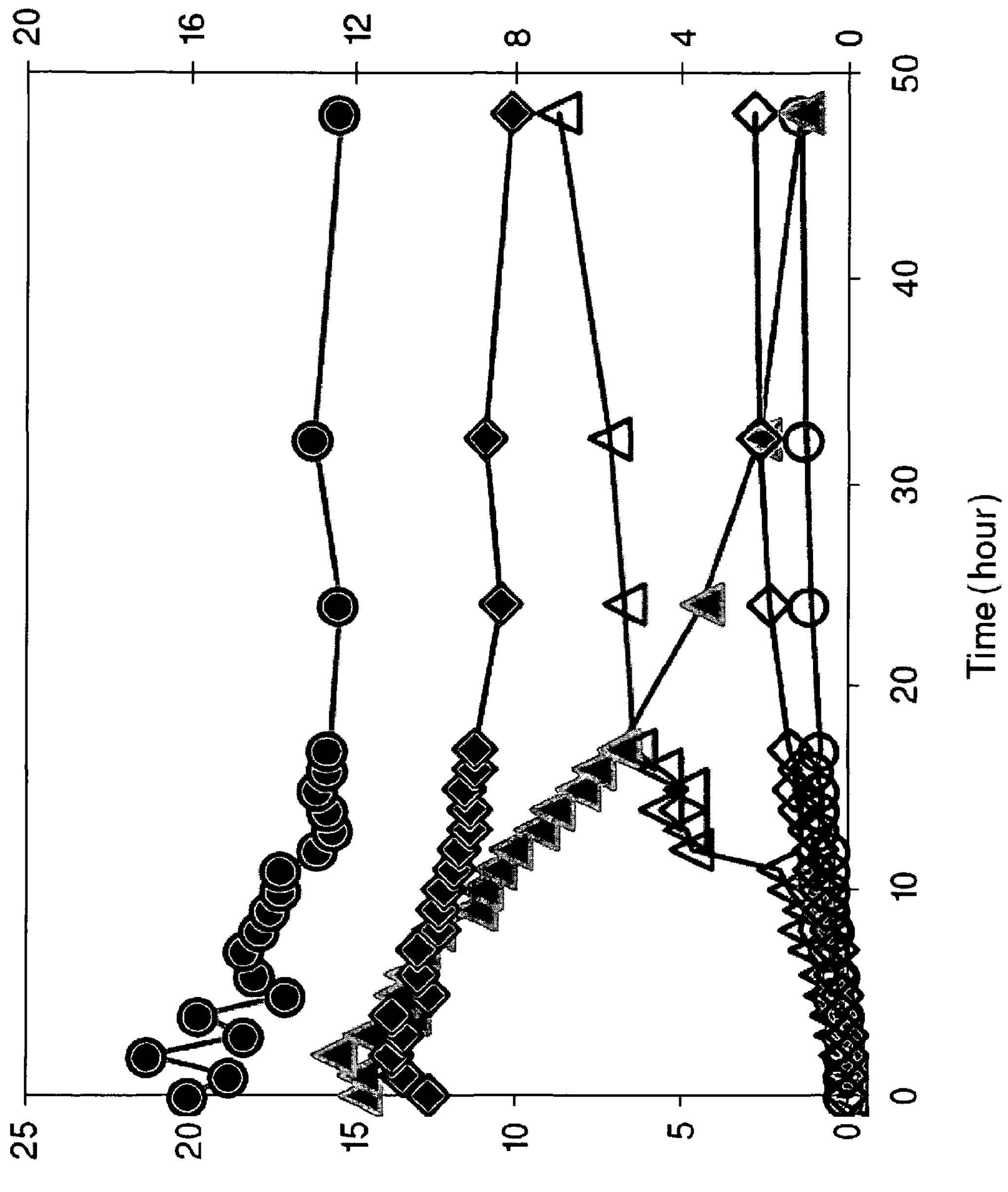
FIG. 4*a*. depicts a graph of *Saccharomyces cerevisiae* NRRL Y-12632 including glucose (●), ethanol (○), HMF (♦), FDM (◇), furfural (▲), and FM (Δ) in the presence of furfural and HMF at 12 mM each on a yeast medium described infra as measured by HPLC analysis. Glucose and ethanol were estimated by g/L (left axis) and the remaining values presented by mM (right axis).
Figure 4B:
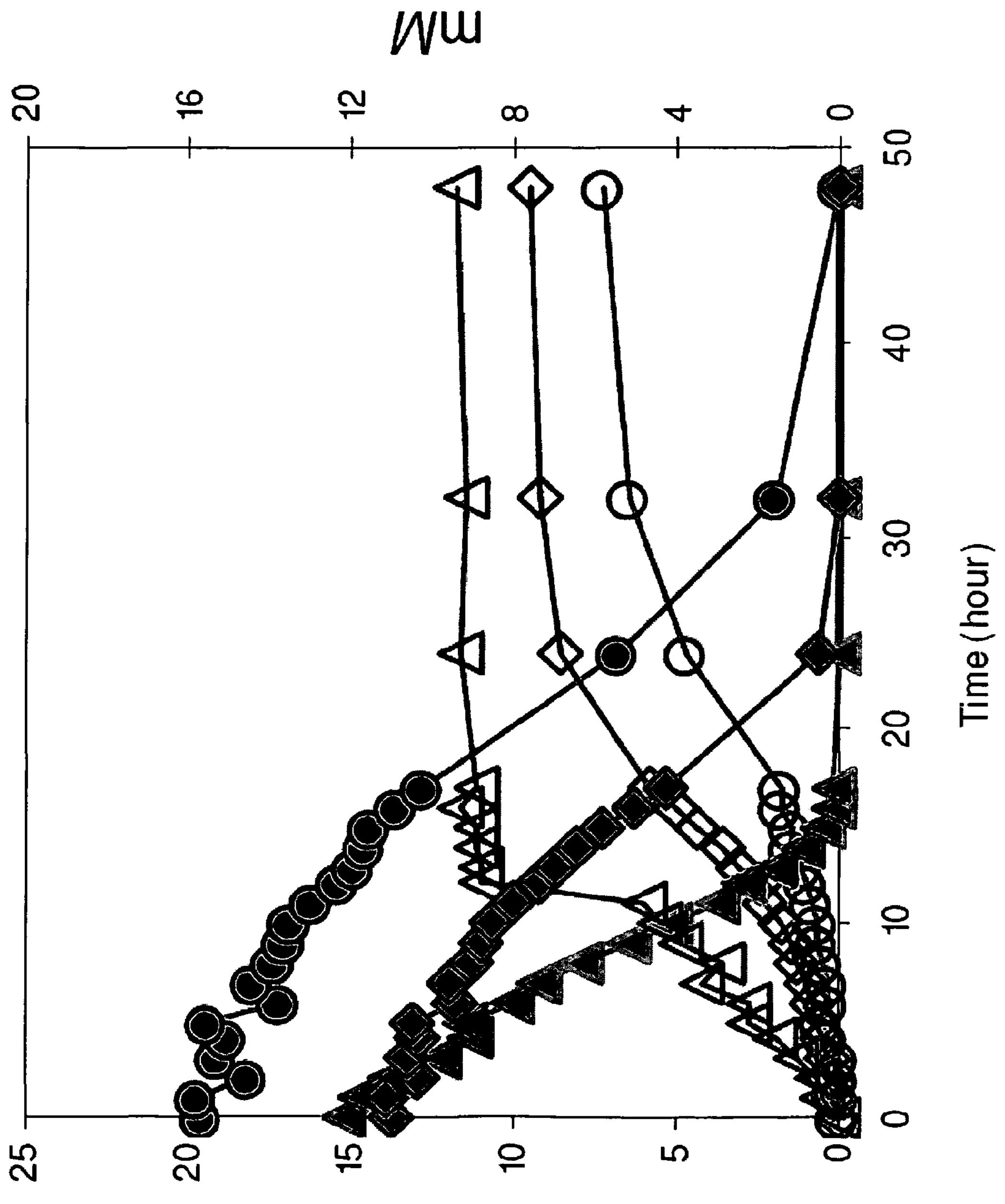
FIG. 4*b* depicts the same variables for strain NRRL Y-50049.
Figure 5A:
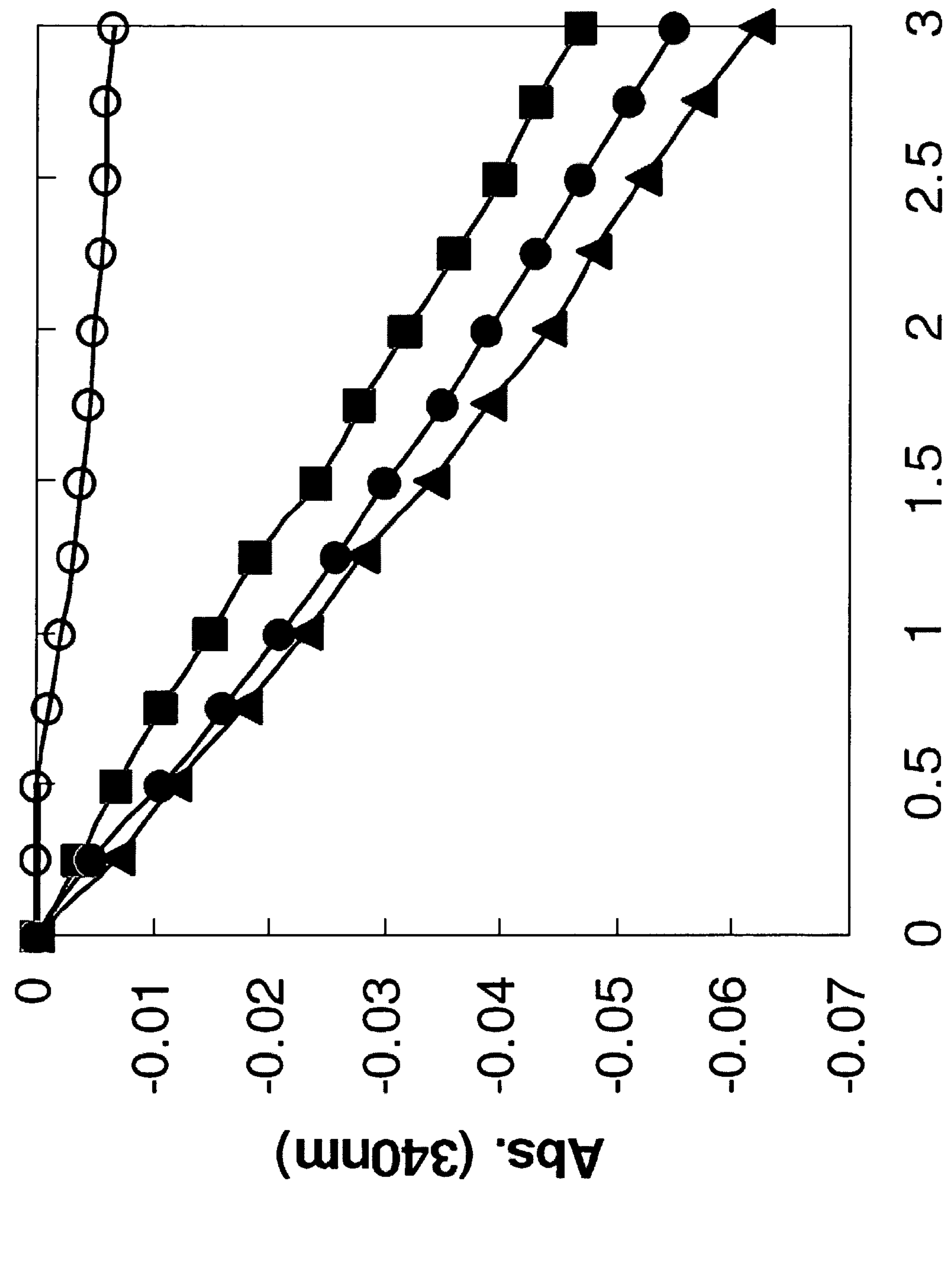
FIG. 5*a*. depicts a graph of enzyme assay of whole cell for *Saccharomyces cerevisiae* NRRL-Y-50049 induced by 30 mM each of furfural (▲), HMF (■), furfural plus HMF (●), and a non inducing treatment (○) showing coupled enzymatic activities with 100 μM of cofactor NADPH with 10 mM of substrate furfural as measured by absorbance at 340 nm as a function of time.
Figure 5B:
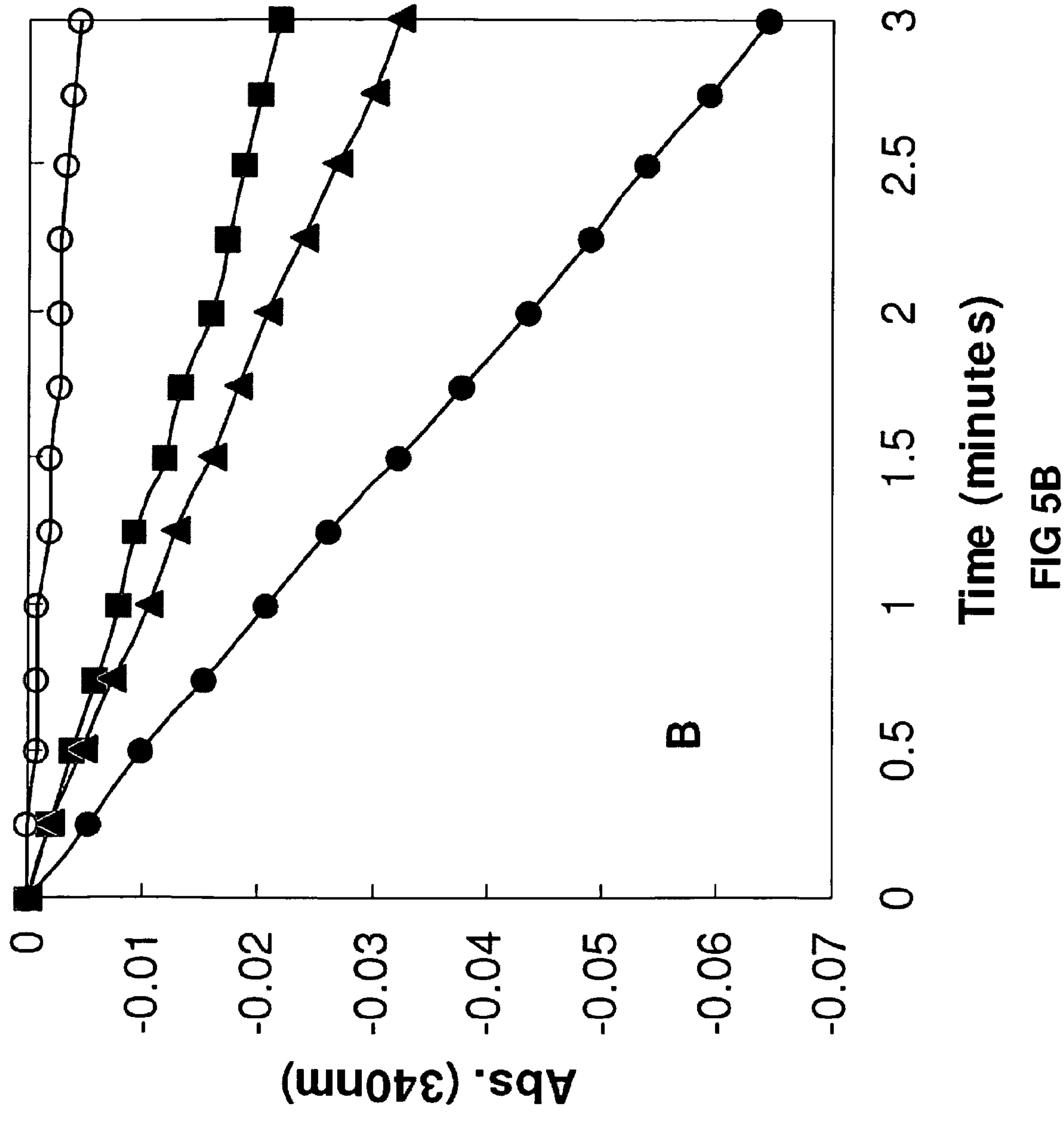
FIG. 5*b*. depicts a graph of enzyme assay of whole cell for NRRL-Y-50049 induced by 30 mM each of furfural (▲), HMF (■), furfural plus HMF (●), and a non inducing treatment (○) showing coupled enzymatic activities with 100 μM of cofactor NADH with 10 mM of substrate furfural as measured by absorbance at 340 nm as a function of time.
Figure 6:
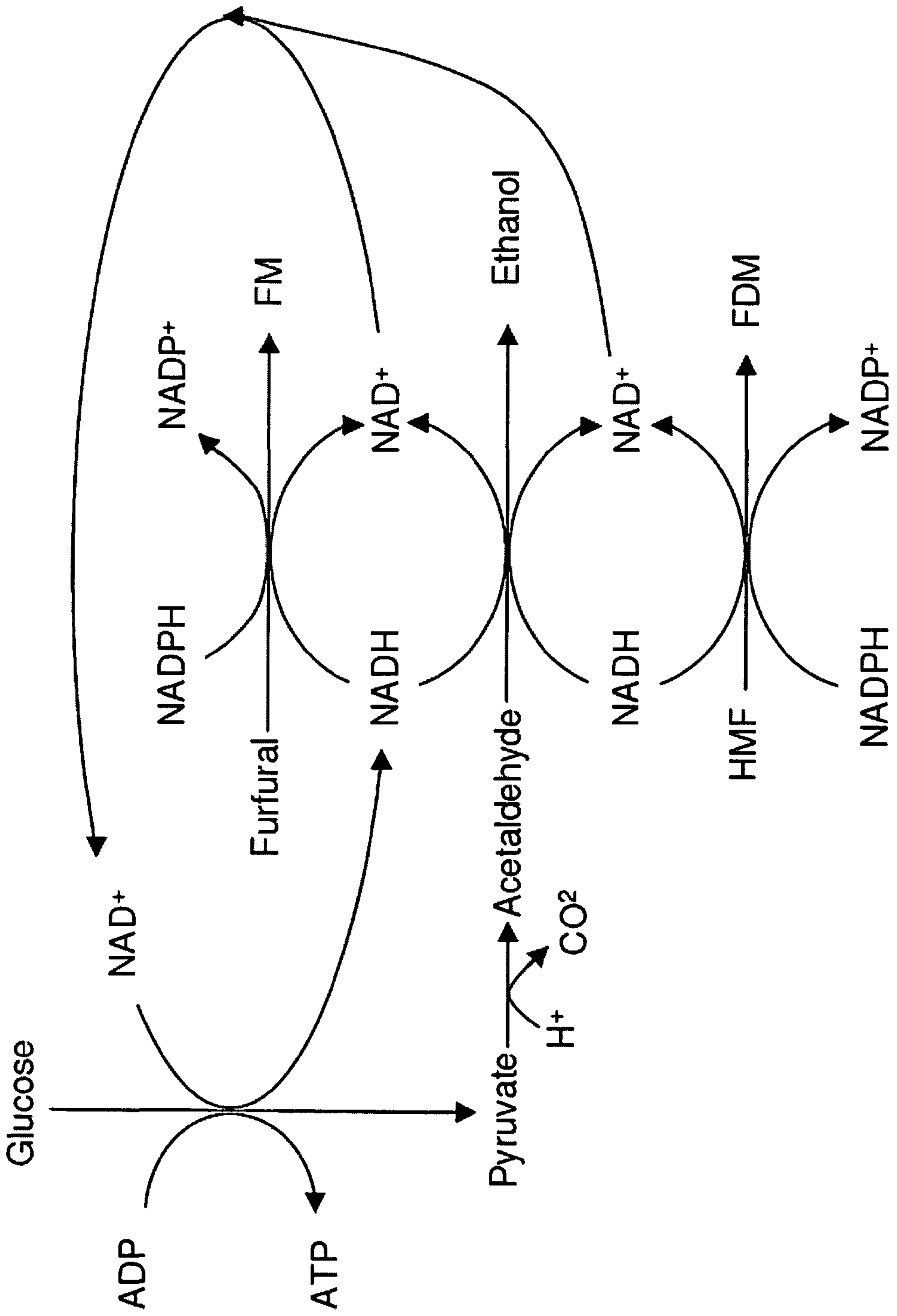
FIG. 6. depicts the furfural and HMF conversion pathways. A schematic diagram shows furfural conversion into furan methanol (FM) and HMF into 2,5-furan-dimethanol (FDM) relative to glycolysis and ethanol production from ethanologenic yeast *Saccharomyces cerevisiae.*

In the initial culture system supplemented with HMF and furfural at a final concentration of 12 mM each, the wild type control Y-12632 was unable to establish a culture at 74 h, whereas the tolerant stain Y-50049 showed a nearly normal cell growth and entered stationary phase at 24 h and completed fermentation within 48 h (FIG. 3). Metabolic activities of strain Y-12632 were repressed and little glucose consumed and ethanol produced (FIG. 4A). Furfural was slowly reduced and HMF remained and almost no conversion activity was observed. In contrast, strain Y-50049 dramatically reduced furfural, and FM reached high concentrations at 12 h (FIG. 4B). At 15 hours, furfural was completely depleted and undetectable. HMF reduction was observed at a much faster rate parallel to glucose consumption. At 32 hours, HMF was completely converted to FDM. Glucose was consumed and ethanol fermentation completed at or prior 48 hours. The inhibitor conversion products FM and FDM remained at the end of the fermentation along with ethanol (FIG. 4B).

EXAMPLE 2 mRNA Expression of Y-50049

Strain Y-50049 was evaluated for whole cell enzyme activities in response to the inhibitor stress. Two 500-ml flasks containing 100 mL of YM media with 2% glucose were inoculated with a 1% inoculum of Y-50049 cells. Samples were incubated in an Innova 4200 incubator (New Brunswick, Edison, N.J.) at 250 rpm for 17 hours at 30° C. when cell cultures reached 0.4 at $OD_{600}$. Then 40 mL of the culture was removed from each flask and divided equally into four 15-ml conical tubes with 10 ml cultures each. These samples were used for enzyme activity assays. The remaining 60 ml culture was used for mRNA expression assays. HMF and furfural were added to the remaining 60 ml of culture in one flask giving a final concentration of 30 mM for each inhibitor. A culture grown under the same conditions by adding the same amount of non-inhibitor diluents served as a control. Cells were harvested 3 h after the inhibitor treatment by centrifugation at room temperature at 2,400×g for 5 min. The supernatant was removed and the pellet washed with a 100 mM phosphate buffer (pH 7.2). The pellets were immediately frozen on dry ice and stored at −80° C.

Enzyme Assay

For enzyme assay, cell cultures in the 15-ml conical tubes were each treated with furfural and/or HMF to reach the following concentrations: 30 mM HMF, 30 mM furfural, 30 mM HMF and 30 mM furfural, and non inhibitor containing culture, which served as a control. After 3 more hours of incubation, the cells were harvested at 2,400×g for 5 minutes at room temperature. Y-50049 cells were lysed using Y-PER® 248 Plus reagent (Pierce, Rockford, Ill.). Cell pellets were resuspended in the lysis solution and incubated at 25° C. with vigorous shaking for 20 minutes. The solution was then centrifuged at 20° C. at 18,000×g to pellet the cells. The supernatant was saved and kept on ice. The lysis procedure was carried out twice following instructions of the manufacturer, and the supernatants were combined. Cell lysates were stored at 4° C. and all samples were used within 2 days for enzyme activity assays.

Protein concentrations for all samples were evaluated using Quick Start™ Bradford Dye Reagent at 595 nm (Bio-Rad Laboratories, Hercules, Calif.) prior the enzyme assay. A standard curve was created using bovine serum albumin. A minimum of 20 μl of each sample was used to determine total protein concentration in the lysate. These protein concentrations were used to determine the amount of each sample to be used for enzyme activity assay.

Cell lysates were assayed for activity using a Genesys 10 uv spectrophotometer (Thermo Scientific, Waltham, Mass.). Activity was monitored by measuring a decrease in absorbance at 340 nm using cofactor NADH and NADPH. Assays were carried out in 500 μl volumes at 25° C. for duration of 3 minutes. The reactions consisted of a final concentration of 10 mM HMF or furfural substrate and 100 μM of cofactor in 100 mM potassium phosphate buffer pH 7.2. All reagents were maintained in a 25° C. water bath prior to use. Cell lysates were kept on ice till used. Activities of whole cell lysates were assayed using 200 μg of extract, and for the overexpressed gene clones, 150 μg protein extract used to start each reaction. The spectrophotometer was blanked before each assay using the reaction mixture as stated above without addition of the lysate. All experiments and assays were run in duplicate.

Furfural and HMF reduction activities of yeast whole cell extracts can be induced by inhibitor treatment of furfural, HMF, and combined treatment of furfural plus HMF. When 10 mM of furfural was used as a substrate, furfural reduction activity coupled with cofactor NADPH by all three treatments was observed to be significantly stronger than the untreated control (FIG. 8A). Among which, furfural induced treatment showed the strongest activities while HMF treated ranked the least. With cofactor NADH, the strongest furfural reduction activity was observed by the induced treatment of furfural plus HMF (FIG. 8B). Such acquired reduction activity did not show a strong cofactor preference between NADH and NADPH on substrate furfural. In contrast, the acquired reduction activity by furfural treatment showed NADPH preference than NADH. Reduction activities acquired by HMF treatment were also higher coupled with NADPH than with NADH. Similar results were obtained by using 10 mM of substrate HMF (data not shown). Cell extracts of the untreated controls showed no significant activities with either cofactor on all substrates.

While the invention has been described with reference to details of the illustrated embodiment, these details are not intended to limit the scope of the invention as defined in the appended claims.

The embodiment of the invention in which exclusive property or privilege is claimed is defined as follows:

1. An isolated *Saccharomyces cerevisiae* strain having been deposited with the United States Department of Agriculture, Agricultural Research Patent Culture Collection as Accession No. NRRL Y-50049, wherein said *Saccharomyces*

*cerevisiae* strain is capable of in situ detoxification of said furfural and 5-hydroxymethylfurfural via aldehyde reduction while producing ethanol.

2. A method of producing ethanol comprising culturing *Saccharomyces cerevisiae* yeast strain NRRL Y-50049 under suitable conditions for a period of time sufficient to allow fermentation of at least a portion of feedstock to produce ethanol, wherein said feedstock contains woody material.

3. The method of claim 2, wherein said woody material is cellulosic or lignocellulosic plant material selected from the group consisting of orchard prunnings, chaparral, mill waste, urban wood waste, municipal waste, logging waste, forest thinnings, short-rotation woody crops, and industrial waste.

4. The method of claim 2, wherein said feedstock is a nonwoody material.

5. The method of claim 4, wherein said nonwoody material is gramineous agricultural residue.

6. The method of claim 4, wherein said nonwoody material is selected from the group consisting of wheat straw, oat straw, rice straw, barley straw, rye straw, flax straw, sugar cane, corn stover, corn stalks, corn cobs, corn husks, prairie grass, switchgrass, gamagrass, and foxtail.

7. The method of claim 4, wherein said nonwoody material is selected from the group consisting of sugar beet pulp, citrus fruit pulp, seed hulls, cellulosic animal wastes, lawn clippings, and seaweed.

* * * * *